(12) United States Patent
Ishihara et al.

(10) Patent No.: US 11,071,600 B2
(45) Date of Patent: Jul. 27, 2021

(54) MEDICAL TREATMENT TOOL AND SURGICAL SYSTEM

(71) Applicant: MEDICAROID CORPORATION, Kobe (JP)

(72) Inventors: Kazuki Ishihara, Kobe (JP); Kenji Ago, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 234 days.

(21) Appl. No.: 15/964,672

(22) Filed: Apr. 27, 2018

(65) Prior Publication Data
US 2018/0311000 A1  Nov. 1, 2018

(30) Foreign Application Priority Data
May 1, 2017 (JP) ............................... JP2017-91235

(51) Int. Cl.
*A61B 34/30* (2016.01)
*A61B 17/28* (2006.01)
*A61B 34/00* (2016.01)

(52) U.S. Cl.
CPC .......... *A61B 34/30* (2016.02); *A61B 17/2812* (2013.01); *A61B 34/71* (2016.02); *A61B 2034/305* (2016.02); *A61B 2034/306* (2016.02)

(58) Field of Classification Search
CPC ......... A61B 34/30; A61B 34/70; A61B 34/71; A61B 2034/305; A61B 2034/306; A61B 17/2812; A61B 17/2816; A61B 2017/2926; A61B 2017/2937; A61B 2017/2947; A61B 2034/715
See application file for complete search history.

(56) References Cited

U.S. PATENT DOCUMENTS

| | | | |
|---|---|---|---|
| 6,394,998 B1 | 5/2002 | Wallace et al. |
| 6,902,560 B1 | 6/2005 | Morley et al. |
| 6,936,042 B2 | 8/2005 | Wallace et al. |
| 7,935,130 B2 | 5/2011 | Williams |
| 9,078,684 B2 | 7/2015 | Williams |
| 9,492,233 B2 | 11/2016 | Williams |
| 2008/0287862 A1 | 11/2008 | Weitzner et al. |
| 2009/0138006 A1 | 5/2009 | Bales et al. |

(Continued)

FOREIGN PATENT DOCUMENTS

| | | |
|---|---|---|
| CN | 202520781 U | 11/2012 |
| JP | 2011-045500 A | 3/2011 |

(Continued)

*Primary Examiner* — Diane D Yabut
(74) *Attorney, Agent, or Firm* — Metrolex IP Law Group, PLLC

(57) ABSTRACT

A compact medical treatment tool having an end portion, used for surgery, and a surgical system having such a medical treatment tool are provided. A medical treatment tool includes an end effector, a wrist member, a shaft, a first pulley, and a second pulley. A first pulley portion included in the end effector is rotatably mounted on the wrist member via a first connection, and is located closer to a first end of the first connection. The first pulley is mounted on the wrist member. A rotational axis of the first pulley intersects with a plane defined by a shaft axis and a first axis that is defined by the first connection. The rotational axis of the first pulley is located closer to a second end of the first connection, opposite to the first end of the first connection, than a groove of the first pulley portion.

20 Claims, 12 Drawing Sheets

(56) References Cited

U.S. PATENT DOCUMENTS

| | | |
|---|---|---|
| 2010/0004663 A1 | 1/2010 | Murphy et al. |
| 2010/0016852 A1 | 1/2010 | Manzo et al. |
| 2010/0168721 A1 | 7/2010 | Rogers et al. |
| 2014/0005704 A1 | 1/2014 | Vakharia et al. |
| 2015/0150635 A1 | 6/2015 | Kilroy et al. |
| 2015/0209965 A1 | 7/2015 | Low et al. |
| 2015/0313676 A1 | 11/2015 | Deodhar |
| 2016/0346001 A1 | 12/2016 | Vakharia et al. |
| 2017/0165012 A1 | 6/2017 | Chaplin et al. |
| 2017/0245842 A1 | 8/2017 | Ito et al. |

FOREIGN PATENT DOCUMENTS

| | | |
|---|---|---|
| JP | 2013-230299 A | 11/2013 |
| JP | 2015-524683 A | 8/2015 |
| JP | 2016-518160 A | 6/2016 |
| JP | 2016-195791 A | 11/2016 |
| WO | 00/30551 A1 | 6/2000 |
| WO | 00/30551 A1 | 11/2000 |
| WO | 2016/080180 | 5/2016 |
| WO | 2017/098270 A1 | 6/2017 |
| WO | 2017/098279 A1 | 6/2017 | form
MEDICAL TREATMENT TOOL AND SURGICAL SYSTEM

CROSS-REFERENCE TO RELATED APPLICATION

This application claims priority to Japanese Patent Application No. 2017-91235 filed on May 1, 2017, the entire contents of which is incorporated herein by reference.

TECHNICAL FIELD

One or more embodiments relate to a medical treatment tool having an end portion, such as a grasping forceps, used for surgery, and a surgical system.

BACKGROUND ART

In recent years, surgical robots have been used in the field of surgery using an endoscope. A surgical robot has a patient-side apparatus which includes a manipulator, and an operating apparatus.

An appropriate medical treatment tool is attached to the manipulator. The medical treatment tool is remote controlled by the operating apparatus to carry out surgery.

As an example of the medical treatment tool as used in the surgical robot, U.S. Pat. No. 6,902,560 (Patent Document 1), for example, discloses a medical treatment tool which has an end portion rotatable about three different axes: roll, pitch, and yaw axes.

SUMMARY

In surgery using such a medical treatment tool, such as when suturing an organ in the body of a patient, it is preferable that an intended procedure can be carried out in a smaller space of the patient's body to avoid contact of the end portion with the organ. It is therefore desired to downsize the medical treatment tool.

One or more embodiments are therefore intended to provide a compact medical treatment tool having an end portion, such as a grasping forceps, used for surgery, and a surgical system having such a medical treatment tool.

To achieve the above objective, a medical treatment tool according to one or more embodiments may include: an end effector including a first pulley portion; a wrist member which extends in a particular direction and on which the first pulley portion is rotatably mounted via a first connection at a first end of the wrist member in the particular direction; a shaft which has a shaft axis and on which a second end of the wrist member, opposite to the first end in the particular direction, is rotatably mounted via a second connection; a first pulley mounted on the wrist member; and a second pulley which is located closer to the second end of the wrist member than the first pulley with respect to the particular direction, and which has a rotational axis parallel to a second axis defined by the second connection. The first pulley portion may be located closer to a first end of the first connection with respect to a first axis defined by the first connection, and may be provided with a groove extending in a circumferential direction of the first pulley portion. The first pulley and the second pulley may stay on one side of a plane defined by the shaft axis and the first axis when the wrist member is in a position in which the particular direction of the wrist member is parallel to the shaft axis. A rotational axis of the first pulley and the rotational axis of the second pulley may intersect with the plane. The rotational axis of the first pulley may be located closer to a second end of the first connection, opposite to the first end of the first connection, than the groove of the first pulley portion.

To achieve the above objective, a medical treatment tool according to one or more embodiments may include: a wrist member extending in a particular direction; an end effector mounted on a first end, in the particular direction, of the wrist member via a first connection; and a shaft. The end effector may be pivotable about a first axis defined by the first connection. A second end of the wrist member, opposite to the first end in the particular direction, may be mounted on an end of the shaft via a second connection. The wrist member may be pivotable about a second axis defined by the second connection. The first axis and the second axis may intersect with each other in plan view from the end effector. A length from the first connection to the second connection may be less than 8 mm.

DETAILED DESCRIPTION

[Surgical System]

Figure 1:
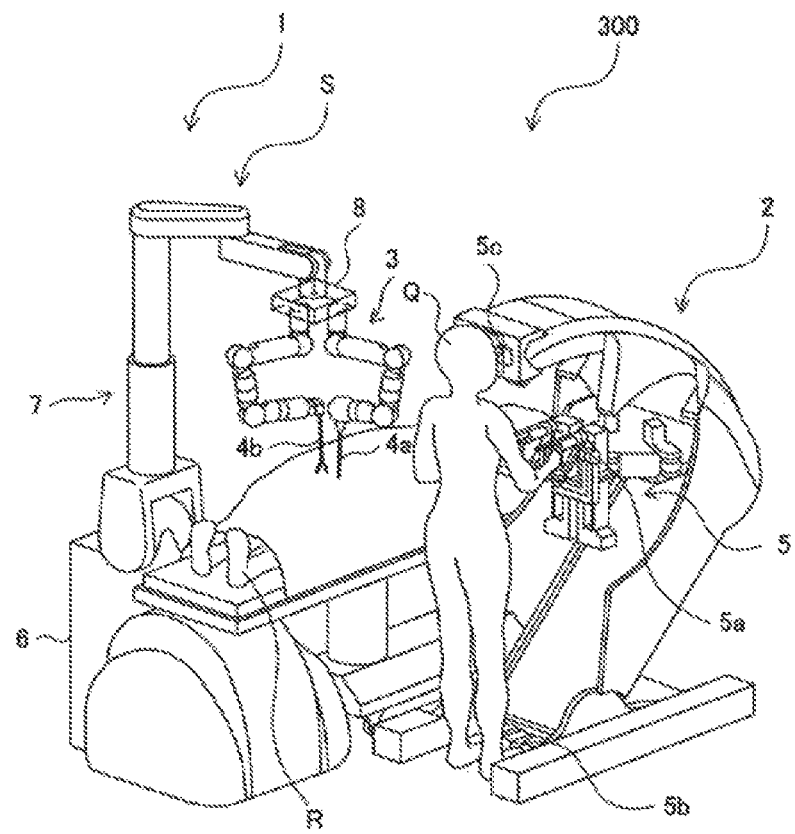
FIG. 1 is a diagram illustrating a configuration of a surgical system according to one or more embodiments.

FIG. 1 is a diagram illustrating a configuration of a surgical system of one or more embodiments.

Referring to FIG. 1, a surgical system 300 is used, for example, to carry out a surgical operation on a treatment target R, such as a human or an animal, using an endoscope operated by an operator Q through a patient-side apparatus 1. The surgical system 300 has the patient-side apparatus 1 and an operating apparatus 2 which operates the patient-side apparatus 1.

The operator Q inputs, to the operating apparatus 2, a movement instruction for the patient-side apparatus 1. The operating apparatus 2 transmits an instruction signal which includes this movement instruction to the patient-side apparatus 1. The patient-side apparatus 1 receives the instruction signal transmitted from the operating apparatus 2, and moves an endoscope assembly 4a and a medical treatment tool 4b connected to the distal end of the patient-side apparatus 1, based on the movement instruction included in the instruction signal received.

More specifically, the operating apparatus 2 includes an operation input section 5 which has a control manipulator 5a and an operation pedal 5b, and a monitor 5c which displays an image taken by the endoscope assembly 4a. The control manipulator 5a and the operation pedal 5b are equipment through which the operator Q inputs the movement instruction.

The operator Q operates the control manipulator 5a and the operation pedal 5b to input the movement instruction to the operating apparatus 2, while viewing an image of the target site displayed on the monitor 5c. The operating apparatus 2 transmits the instruction signal, which includes the input movement instruction, to the patient-side apparatus 1 through a wired or wireless connection.

The patient-side apparatus 1 includes: a positioner 7; a platform 8 attached to an end of the positioner 7; a plurality of manipulators 3 detachably attached to the platform 8; the endoscope assembly 4a; the medical treatment tool 4b; and a controller 6 which controls the movement of the patient-side apparatus 1.

The endoscope assembly 4a and the medical treatment tool 4b are attached to the manipulators 3. The controller 6 receives the instruction signal transmitted from the operating apparatus 2, and moves the endoscope assembly 4a and the medical treatment tool 4b, based on the instruction signal received.

Specifically, the controller 6 which has received the instruction signal first moves the positioner 7, thereby positioning the platform 8, based on the movement instruction included in the instruction signal. The controller 6 positions the manipulators 3, too, such that the endoscope assembly 4a and the medical treatment tool 4b take predetermined initial positions with respect to cannulas, not shown, retained on the body surface of the treatment target R.

Then, the controller 6 outputs, based on the movement instruction, a control signal for activating the endoscope assembly 4a and the medical treatment tool 4b to the endoscope assembly 4a and the medical treatment tool 4b via the manipulators 3. The endoscope assembly 4a and the medical treatment tool 4b move according to the control signal transmitted from the controller 6.

The controller 6 does not need to be embedded in the positioner 7, and may be provided independently of the positioner 7.

[General Configuration of Medical Treatment Tool]

Figure 2:
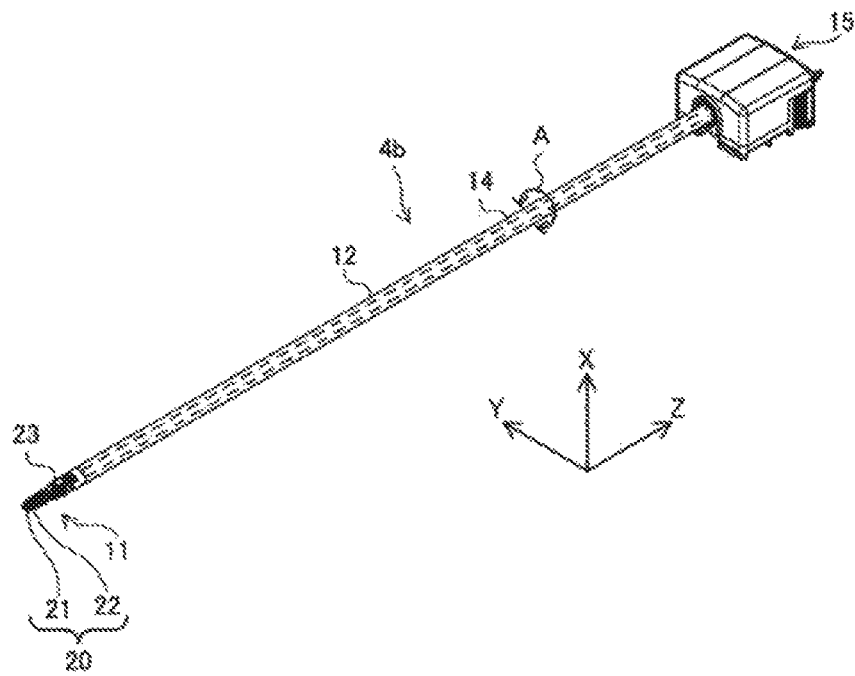
FIG. 2 is a diagram illustrating a configuration of a medical treatment tool according to one or more embodiments.

FIG. 2 is a diagram illustrating a configuration of a medical treatment tool according to one or more embodiments.

Referring to FIG. 2, the medical treatment tool 4b includes an end portion 11, a shaft 12, an elongate element 14 (e.g., a plurality of wires or cable) for operating the end portion 11, and an activation mechanism 15 which activates the elongate element 14.

Examples of the end portion 11 include a grasping forceps (i.e., a grasper), a needle holder (i.e., a needle driver) or a pair of scissors. Now, a case in which the end portion 11 is a grasping forceps will be described.

The end portion 11 includes an end effector 20 and a wrist member 23 extending in a particular direction, that is, in a longitudinal direction of the medical treatment tool 4b. The end effector 20 has two jaws 21 and 22, for example. The two jaws 21 and 22 having the same shape can reduce the fabrication costs.

The shaft 12 has a tubular shape extending in the longitudinal direction of the medical treatment tool 4b, and is rotatable in the directions indicated by the arrows A. That is, the shaft 12 is rotatable about an axis extending in its own longitudinal axis (i.e., about a shaft axis).

The elongate element 14 is made, for example, of tungsten or stainless steel to provide sufficient strength, bendability, and durability. Stainless steel is softer, but stretches more easily, than tungsten. Tungsten is harder, but is less likely to stretch, than stainless steel.

The activation mechanism 15 is mounted on one of the manipulators 3 of the patient-side apparatus 1 illustrated in FIG. 1. The activation mechanism 15 receives the control signal from the patient-side apparatus 1 via the manipulator 3. Based on this control signal, the activation mechanism 15 moves the elongate element 14 along the longitudinal direction of the medical treatment tool 4b and/or rotates the shaft 12 in the directions indicated by the arrows A.

[End Portion]

(General Configuration of End Portion)

Figure 3:
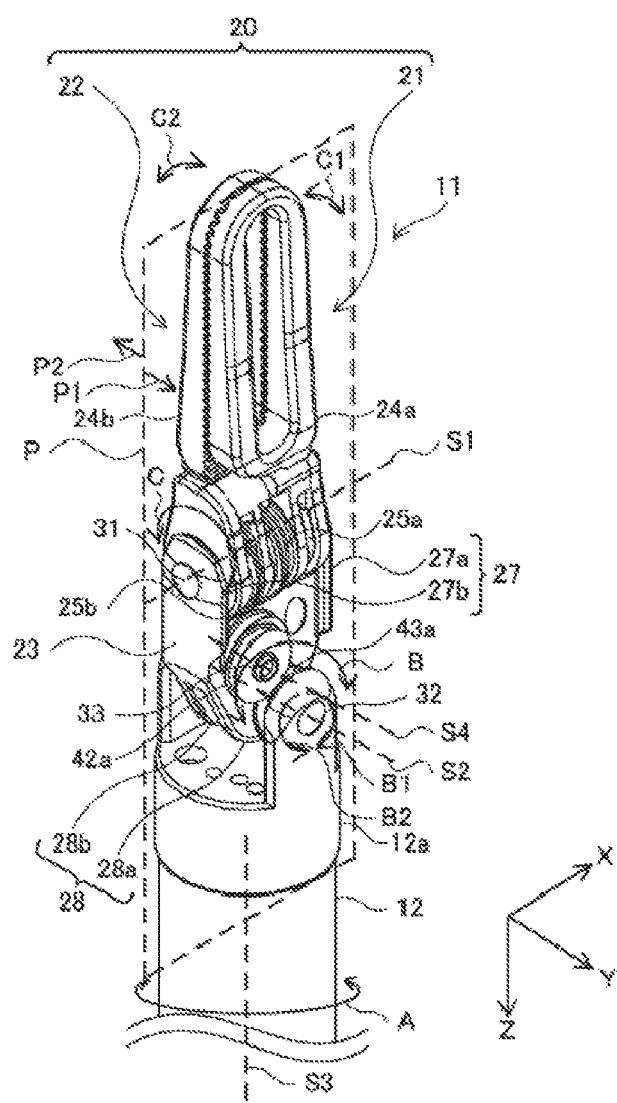
FIG. 3 is a diagram illustrating a perspective view of a configuration of an end portion of the medical treatment tool according to one or more embodiments.

FIG. 3 is a diagram illustrating a perspective view of a configuration of the end portion of the medical treatment tool according to one or more embodiments.

Referring to FIG. 3, the end portion 11 also has a first connection 31 and a second connection 32, in addition to the end effector 20 and the wrist member 23. The first and second connections 31 and 32 are bolts or screws, for example.

In the following description, an axis parallel to a first axis S1 defined by the first connection 31 will be referred to as an X-axis. An axis parallel to a second axis S2 defined by the second connection 32 will be referred to as a Y-axis. An axis parallel to a third axis (i.e., the shaft axis) S3 defined by the shaft 12 will be referred to as a Z-axis.

The extending direction of the first axis S1 may be slightly shifted from the extending direction of the first connection 31. The extending direction of the second axis S2 may be slightly shifted from the extending direction of the second connection 32. The extending direction of the third axis S3 may be slightly shifted from the extending direction of the shaft 12.

Preferably, the first axis S1 and the second axis S2 intersect with each other in plan view from the end effector 20 (i.e., in plan view from the negative to positive side of the Z-axis). That is, the first, second, and third axes S1, S2, and S3 extend in directions different from one another. In this embodiment, each of an angle formed by the first axis S1 and the second axis S2, an angle formed by the first axis S1 and the third axis S3, and an angle formed by the second axis S2 and the third axis S3 is 90 degrees.

The wrist member 23 has a clevis 27 positioned at a first end closer to the end effector 20 in the Z-axis direction, and a clevis 28 positioned at a second end closer to the shaft 12 in the Z-axis direction. The clevis 28 closer to the wrist member 23 is mounted on an end 12a of the shaft 12 via the second connection 32. The wrist member 23 is pivotable about the second axis S2 in the directions indicated by the arrows B.

The jaws 21 and 22 are mounted on the clevis 27 of the wrist member 23 via the first connection 31. The jaws 21 and 22 have finger portions 24a and 24b and pulley portions 25a and 25b, respectively. The pulley portions 25a and 25b are rotatable about the first axis S1. Each of the pulley portions 25a and 25b is provided with a groove in a circumferential direction thereof, around which groove the elongate element 14 is wound.

The finger portion 24a has an elongated shape extending from the pulley portion 25a. The finger portion 24b has an elongated shape extending from the pulley portion 25b. The finger portion 24a and the pulley portion 25a are formed integrally, for example. The finger portion 24b and the pulley portion 25b are formed integrally, for example.

More specifically, the finger portion 24a stays on one side of a plane P defined by the first and third axes S1 and S3 (i.e., on the side indicated by the arrow P1) when the finger portion 24a is in a position in which the longitudinal direction thereof is parallel to the longitudinal direction of the wrist member 23 (i.e., a position parallel to the Z-axis). Further, the finger portion 24b stays on the other side of the plane P (i.e., on the side indicated by the arrow P2) when the finger portion 24a is in a position in which the longitudinal direction thereof is parallel to the Z-axis.

Figure 4:
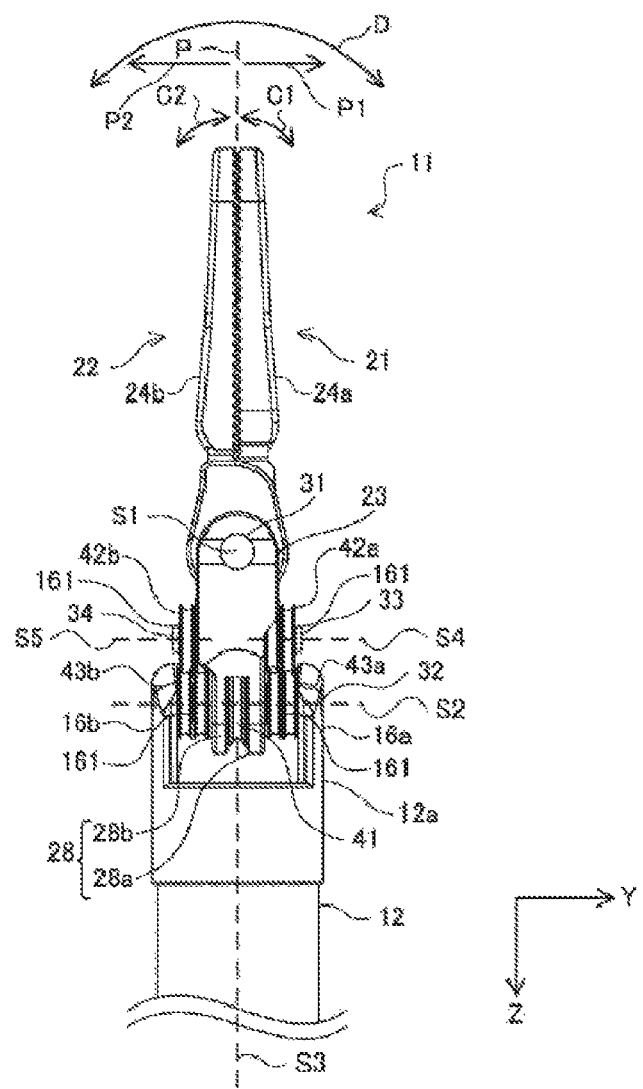
FIG. 4 is a diagram illustrating a side view of the configuration of the end portion of the medical treatment tool according to one or more embodiments.

FIG. 4 is a diagram illustrating a side view of the configuration of the end portion of the medical treatment tool according to one or more embodiments.

Referring to FIG. 4, the jaws 21 and 22 pivot about the first axis S1, and thus can move toward and away from each other or can pivot in the same direction, as indicated by the arrows C1 and C2.

More specifically, the end portion 11 also has a third connection 33, a fourth connection 34, a first pulley 42a, a second pulley 43a, a third pulley 42b, a fourth pulley 43b, and a fifth pulley 41, in addition to the end effector 20, the wrist member 23, the first connection 31, and the second connection 32. The third and fourth connections 33 and 34 are bolts or screws, for example. Each of the first, second, third, and fourth pulleys 42a, 43a, 42b, and 43b has an inner pulley and an outer pulley.

The first and second pulleys 42a and 43a are provided on the one side of the plane P, that is, on the side indicated by the arrow P1, where the finger portion 24a stays. The third and fourth pulleys 42b and 43b are provided on the other side of the plane P, that is, on the side indicated by the arrow P2, where the finger portion 24b stays. The fifth pulley 41 is provided on the plane P, for example.

The second, fourth, and fifth pulleys 43a, 43b, and 41 are mounted on the end 12a of the shaft 12 via the second connection 32, and are rotatable about the second axis S2. This configuration in which the second, fourth, and fifth pulleys 43a, 43b, and 41 are mounted via the same member can reduce the number of components. However, the rotational axes of these pulleys may be slightly shifted as long as the rotational axes are parallel to one another. It is not essential to share the same rotational axis.

Figure 5:
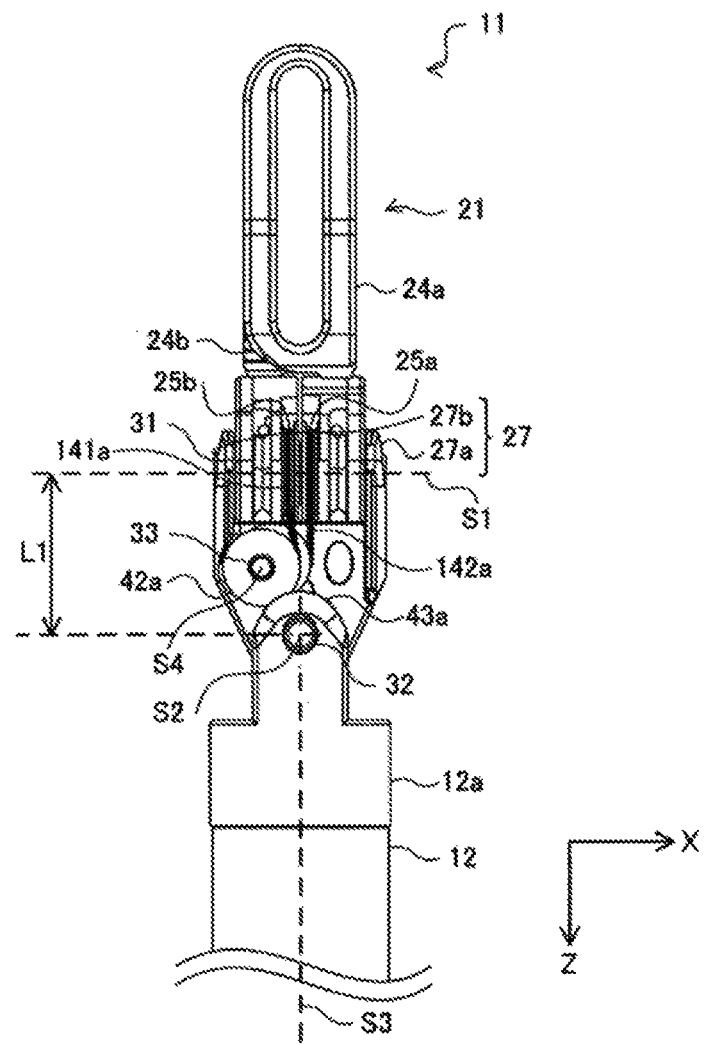
FIG. 5 is a diagram illustrating a front view of the configuration of the end portion of the medical treatment tool according to one or more embodiments.

The first pulley 42a is mounted on the wrist member 23 via the third connection 33, and is rotatable about a fourth axis S4 defined by the third connection 33. The third pulley 42b is mounted on the wrist member 23 via the fourth connection 34, and is rotatable about a fifth axis S5 defined by the fourth connection 34. As illustrated in FIG. 5, the inner and outer pulleys of the first pulley 42a have parallel rotational axes, which however are shifted slightly. Similarly, as illustrated in FIG. 5, the inner and outer pulleys of the third pulley 42b have parallel rotational axes, which however are slightly shifted.

The extending direction of the fourth axis S4 may be slightly shifted from the extending direction of the third connection 33. The extending direction of the fifth axis S5 may be slightly shifted from the extending direction of the fourth connection 34. The fourth axis S4 and the fifth axis S5 intersect with the plane P. For example, each of an angle formed by the fourth axis S4 and the plane P and an angle formed by the fifth axis S5 and the plane P is 90 degrees.

The first pulley 42a is arranged such that the plane of rotation thereof is approximately flush with the plane of rotation of the second pulley 43a. The third pulley 42b is arranged such that the plane of rotation thereof is approximately flush with the plane of rotation of the fourth pulley 43b. For example, the first, second, third, and fourth pulleys 42a, 43a, 42b, and 43b are arranged such that the planes of rotation of all of these pulleys are parallel to the plane P.

FIG. 5 is a diagram illustrating a front view of the configuration of the end portion of the medical treatment tool according to one or more embodiments.

Referring to FIG. 5, the end portion 11 of the medical treatment tool 4b is configured such that the length L1 from the first connection 31 to the second connection 32 is less than 8 mm, e.g., 7.5 mm. In a case where the medical treatment tool 4b is a needle holder, the end portion 11 is configured such that the length L1 is 7 mm.

(Detailed Configuration of End Portion)

Referring again to FIG. 4, the clevis 28 positioned at the end of the wrist member 23 closer to the shaft 12 in the Z-axis direction is U-shaped, for example. The clevis 28 includes a round portion 28a near a first end of the second connection 32 and a round portion 28b near a second end of the second connection 32. For example, each of the round portions 28a and 28b is provided with a through hole (not shown), which the second connection 32 passes through.

The end 12a of the shaft 12 is also U-shaped and includes two round portions 16a and 16b. The round portion 16a is provided on the one side of the plane P, that is, on the side indicated by the arrow P1. The round portion 16b is provided on the other side of the plane P, that is, on the side indicated by the arrow P2. The second pulley 43a is provided between the round portion 28a of the wrist member 23 and the round portion 16a of the shaft 12. The fourth pulley 43b is provided between the round portion 28b of the wrist member 23 and the round portion 16b of the shaft 12.

Referring again to FIG. 5, similarly to clevis 28, the clevis 27 is U-shaped, for example, and includes a round portion 27a near a first end of the first connection 31 and a round portion 27b near a second end of the first connection 31. For example, each of the round portions 27a and 27b is provided with a through hole (not shown), which the first connection 31 passes through.

The pulley portion 25a is provided between the round portions 27a and 27b and near the round portion 27a. The pulley portion 25b is provided between the round portions 27a and 27b and near the round portion 27b.

The fourth axis S4, which is a rotational axis of the first pulley 42a, is located closer to the round portion 27b than a groove of the pulley portion 25a in the X-axis direction. Further, the fifth axis S5 illustrated in FIG. 4, which is a rotational axis of the third pulley 42b, is located closer to the round portion 27a than a groove of the pulley portion 25b in the X-axis direction.

Figure 7:
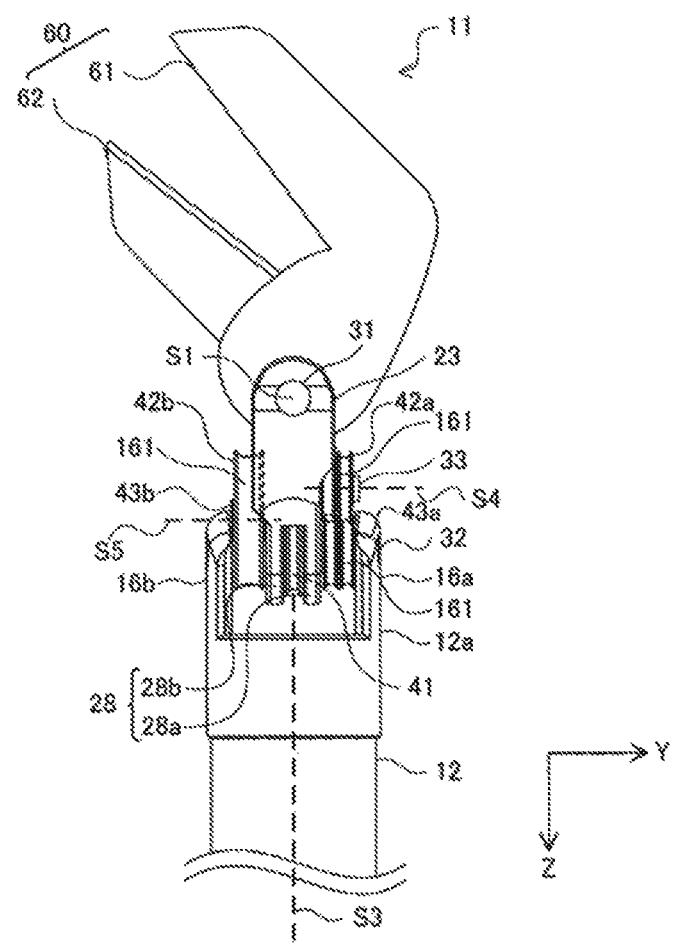
FIG. 7 is a diagram illustrating a side view of a variation of the configuration of the end portion of the medical treatment tool according to one or more embodiments.

Referring to FIG. 5, if the fourth axis S4 were located closer to the round portion 27a, instead of being located closer to the round portion 27b, the distance between the pulley portion 25a and the first pulley 42a would be reduced and the jaw 21 might come into contact with the first pulley 42a when the jaw 21 pivots about the fourth axis S1. Thus, in order to locate the fourth axis S4 near the round portion 27a, the length of the wrist member 23 in the Z-axis direction needs to be increased to increase the distance, and hence avoid contact, between the jaw 21 and the first pulley 42a, as illustrated in FIG. 7 of Patent Document 1.

Moreover, the jaw 21 and the first pulley 42a arranged too close to each other in order to locate the fourth axis S4 near the round portion 27a results in a short length of the elongate element 14 (which is wrapped to cause the jaw 21 to make a pivotal movement) from the groove of the pulley portion 25a of the jaw 21 to the first pulley 42a, and a great angle of the elongate element 14 with respect to the Z-axis. Thus, when the jaw 21 is pivoted in the direction indicated by the arrow P1 in FIG. 4, the elongate element 14 may come off the groove of the pulley portion 25a, and the operation to cause the jaw 21 to make a pivotal movement may be impaired. From this point of view, as well, it is necessary to maintain a distance long enough between the jaw 21 and the first pulley 42a.

On the other hand, the medical treatment tool 4b according to the present example configuration is configured such that the fourth axis S4 is provided near the round portion 27b, as mentioned above. Thus, the jaw 21 does not come into contact with the first pulley 42a even when the jaw 21 makes a pivotal movement. The jaw 21 and the first pulley 42a can thus be located close to each other in the Z-axis direction.

Moreover, even if the jaw 21 and the first pulley 42a are located close to each other in the Z-axis direction as mentioned, the length of the elongate element 14 (which is wrapped to cause the jaw 21 to make a pivotal movement) from the groove of the pulley portion 25a of the jaw 21 to the first pulley 42a is still long. Thus, the elongate element 14 can be prevented from coming off the groove of the pulley portion 25a, and the operation to cause the jaw 21 to make a pivotal movement can be prevented from being impaired.

The length of the wrist member 23 in the Z-axis direction can thus be reduced, and the whole of the end portion 11 can be downsized. The length L1 from the first connection 31 to the second connection 32 can thus be set to about 7 mm, for example.

(Wrapping of Elongate Element)

Figure 6:
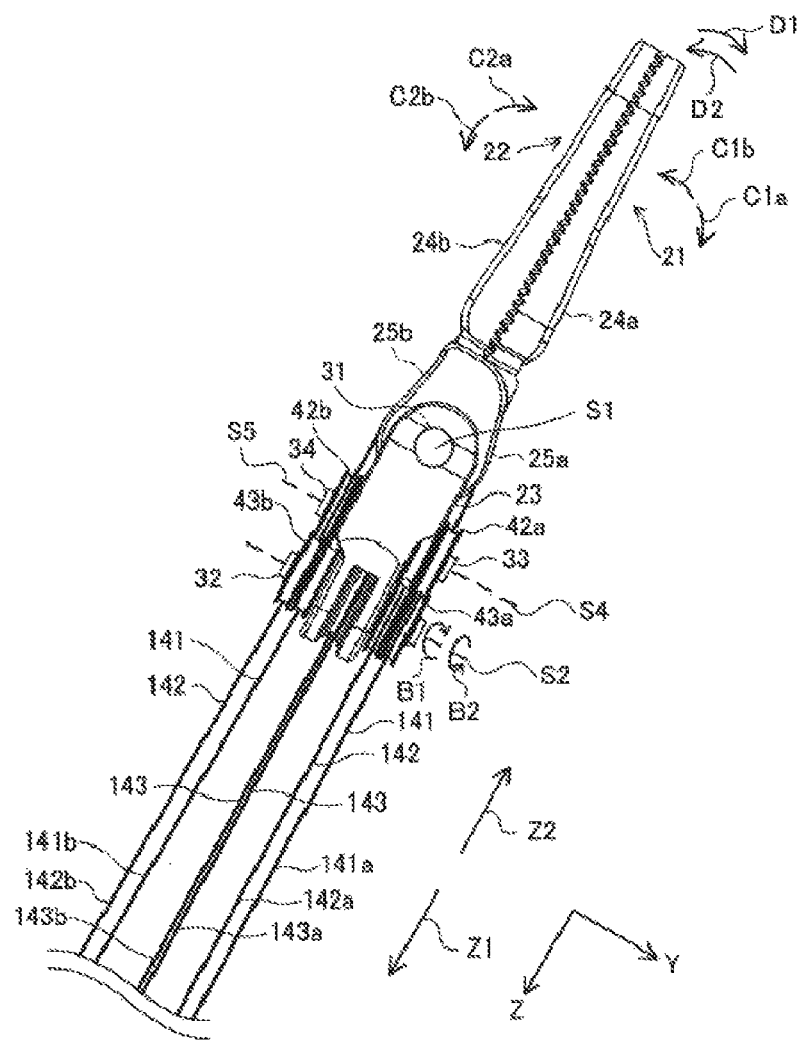
FIG. 6 is a diagram illustrating an example wrapping of an elongate element around the end portion of the medical treatment tool according to one or more embodiments.

FIG. 6 is a diagram illustrating an example wrapping of the elongate element around the end portion of the medical treatment tool of one or more embodiments. In FIG. 6, the arrow Z1 indicates the positive direction of the Z-axis extending parallel to the shaft axis, and the arrow Z2 indicates the negative direction of the Z-axis.

In the present embodiment, the medical treatment tool 4b includes three elongate elements 14. The three elongate elements 14 will be referred to as an elongate element (i.e., a first elongate element) 141, an elongate element (i.e., a first elongate element) 142, and an elongate element (i.e., a second elongate element) 143. The elongate elements 141, 142, and 143 have wires 141a, 142a, and 143a and wires 141b, 142b, and 143b, respectively.

Referring to FIG. 6, the medical treatment tool 4b is assembled as follow: the wire 141a is guided by the pulley portion 25b and is then guided by the outer pulley of the first pulley 42a; and the wire 141a passes through a space between the first pulley 42a and the second pulley 43a and is guided by the outer pulley of the second pulley 43a.

More specifically, referring again to FIG. 5, the wire 141a is guided by the pulley portion 25b and is then guided to the space between the first and second pulleys 42a and 43a from a side closer to the round portion 27a. That is, the wire 141a passes through the space between the first and second pulleys 42a and 43a, while being guided by a portion of the first pulley 42a near the positive side of the X-axis, and is guided by a portion of the second pulley 43a near the negative side of the X-axis.

Referring again to FIG. 6, similarly to the wire 141a, the wire 141b is guided by the pulley portion 25b and is then guided by the inner pulley of the third pulley 42b. The wire 141b passes through a space between the third pulley 42b and the fourth pulley 43b and is guided by the inner pulley of the fourth pulley 43b. The wires 141a and 141b are fixed, for example, to the finger portion 24b of the jaw 22. The jaw 21 therefore moves in conjunction with the actuation of the wires 141a and 141b.

Similarly to the wire 141a, the wire 142a is guided by the pulley portion 25a and is then guided by the inner pulley of the first pulley 42a. The wire 142a passes through the space between the first pulley 42a and the second pulley 43a and is guided by the inner pulley of the second pulley 43a.

Similarly to the wire 141a, the wire 142b is guided by the pulley portion 25a and is then guided by the outer pulley of the third pulley 42b. The wire 142b passes through the space between the third pulley 42b and the fourth pulley 43b and is guided by the outer pulley of the fourth pulley 43b. The wires 142a and 142b are fixed, for example, to the finger portion 24a of the jaw 21. The jaw 21 therefore moves in conjunction with the actuation of the wires 142a and 142b.

The wires 143a and 143b are wrapped around the fifth pulley 41. Further, the wires 143a and 143b are fixed, for example, to the wrist member 23. The wrist member 23 therefore moves in conjunction with the actuation of the wires 143a and 143b.

(Movement of End Portion in Conjunction with Actuation of Elongate Element)

The wire 141a of the elongate element 141, when pulled in the Z1 direction, causes the jaw 22 to pivot in the direction of the arrow C2a, that is, to pivot circumferentially about the first axis S1 toward the jaw 21. The wire 141b of the elongate element 141, when pulled in the Z1 direction, causes the jaw 22 to pivot in the direction of the arrow C2b, that is, to pivot circumferentially about the first axis S1 away from the jaw 21.

The wire 142a of the elongate element 142, when pulled in the Z1 direction, causes the jaw 21 to pivot in the direction of the arrow C1a, that is, to pivot circumferentially about the first axis S1 away from the jaw 22. The wire 142b of the elongate element 142, when pulled in the Z1 direction, causes the jaw 21 to pivot in the direction of the arrow C1b, that is, to pivot circumferentially about the first axis S1 toward the jaw 22.

The wires 141b and 142a, when simultaneously pulled in the Z1 direction, cause the jaws 21 and 22 to pivot circumferentially about the first axis S1 away from each other. The wires 141a and 142b, when simultaneously pulled in the Z1 direction, cause the jaws 21 and 22 to pivot circumferentially about the first axis S1 toward each other.

The wires 141a and 142a, when simultaneously pulled in the Z1 direction, cause both of the jaws 21 and 22 to pivot circumferentially about the first axis S1 in the direction indicated by the arrow D1. That is, the jaw 21 pivots in the C1a direction, and the jaw 22 pivots in the C2a direction.

The wires 141b and 142b, when simultaneously pulled in the Z1 direction, cause both of the jaws 21 and 22 to pivot circumferentially about the first axis S1 in the direction indicated by the arrow D2. That is, the jaw 21 pivots in the C1b direction, and the jaw 22 pivots in the C2b direction.

The wire 143a, when pulled in the Z1 direction, causes the wrist member 23 to pivot in a direction indicated by the arrow B2, that is, to pivot circumferentially about the second axis S2 and counterclockwise as viewed from the negative to positive direction of the Y-axis. The wire 143b, when pulled in the Z1 direction, causes the wrist member 23 to pivot in a direction indicated by the arrow B1, that is, to pivot circumferentially about the second axis S2 and clockwise as viewed from the negative to positive direction of the Y-axis.

In this manner, the jaws 21 and 22 and the wrist member 23 move independently of one another in conjunction with the actuation of the elongate elements 141, 142, and 143. That is, the jaws 21 and 22 rotate about the yaw axis, using the first axis S1 as the yaw axis. The wrist member 23 rotates about the pitch axis, using the second axis S2 as the pitch axis. As mentioned earlier, the shaft 12 illustrated in FIG. 3 rotates about the roll axis, using the third axis S3 as the roll axis.

[Variations of End Portion]

The end portion 11 described above is configured to have two jaws 21 and 22 pivotable about the first axis S1, but is not limited thereto.

FIG. 7 is a diagram illustrating a side view of a variation of the configuration of the end portion of the medical treatment tool according to one or more embodiments.

Referring to FIG. 7, an end effector 60 of the end portion 11 has a jaw 61 pivotable about the first axis S1, and a jaw 62 fixed to the wrist member 23. In this case, the jaw 61 is pivoted about the first axis S1 and is thus capable of moving toward and away from the jaw 62.

In a case where the medical treatment tool 4b is a monopolar hook, a monopolar spatula, or the like, the end effector 60 has one hook portion (not shown) pivotable about the first axis S1 or one spatula portion (not shown), instead of the jaws 61 and 62.

[Activation Mechanism]

Figure 8:
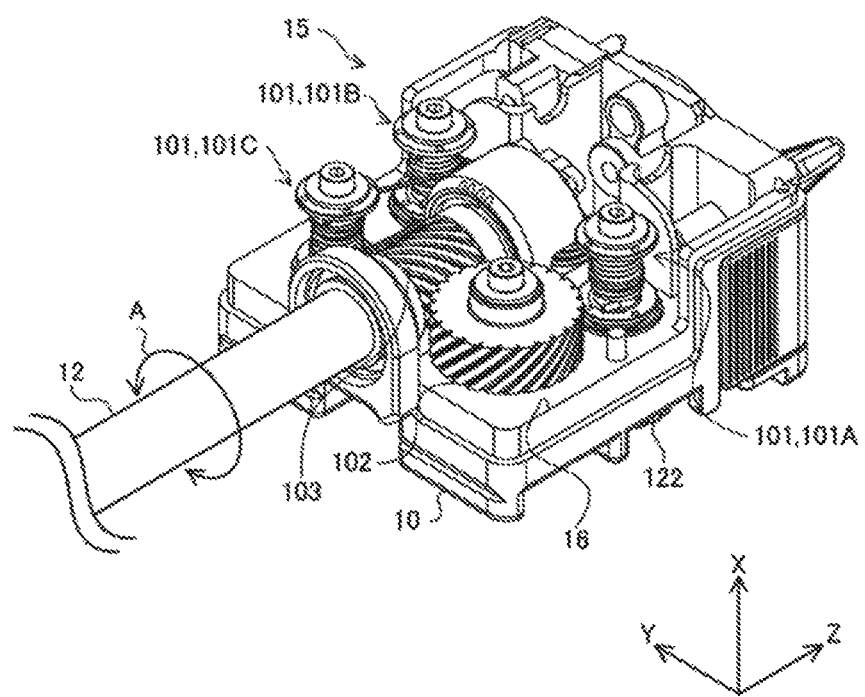
FIG. 8 is a diagram illustrating a perspective view of a configuration of an activation mechanism according to one or more embodiments.

FIG. 8 is a diagram illustrating a perspective view of a configuration of an activation mechanism of one or more embodiments.

Referring to FIG. 8, the activation mechanism 15 has a housing 10, a plurality of activation members 101 rotatably provided in the housing 10, a first gear 102 rotatably provided in the housing 10, a second gear 103 which engages with the first gear 102, and a plurality of transmission members. In FIG. 8, an upper portion of the housing 10 is omitted to illustrate an internal configuration of the activation mechanism 15.

Each of the plurality of activation members 101 and the first gear 102 has a receiving member 122. Each of the plurality of transmission members engages with a corresponding one of these receiving members 122. Each of the plurality of the activation members 101 and the first gear 102 is rotatable about a rotational axis extending in a direction perpendicular to a surface of a base 16, that is, extending in the X-axis direction. The second gear 103 is rotatable about a rotational axis extending in the longitudinal direction of the shaft 12, that is, extending in the Z-axis direction. The shaft 12 engages with the second gear 103, and rotates in the directions indicated by the arrows A in conjunction with the rotation of the second gear 103.

The actuator included in the manipulator 3 illustrated in FIG. 1 receives the control signal from the patient-side apparatus 1. Based on this control signal, the actuator rotates the plurality of transmission members. The rotation of each transmission member causes an associated one of the plurality of activation members 101 and the first gear 102 to rotate.

More specifically, the activation mechanism 15 has three activation members 101. The three activation members 101 will be referred to as an activation member (i.e., a first activation member) 101A, an activation member (i.e., a second activation member) 101B, and an activation member 101C. The elongate elements 141, 142, and 143 illustrated in FIG. 6 are wound around the activation members 101A, 101B, and 101C, respectively.

When the rotation, by the actuator, of the transmission member associated with the activation member 101A causes the activation member 101A to rotate, the elongate element 141 wound around the activation member 101A moves along the Z-axis. Consequently, the jaw 22 illustrated in FIG. 3 pivots in the directions indicated by the arrows C1.

When the rotation, by the actuator, of the transmission member associated with the activation member 101B causes the activation member 101B to rotate, the elongate element 142 wound around the activation member 101B moves along the Z-axis. Consequently, the jaw 21 illustrated in FIG. 3 pivots in the directions indicated by the arrows C2.

When the rotation, by the actuator, of the transmission member associated with the activation member 101C causes the activation member 101C to rotate, the elongate element 143 wound around the activation member 101C moves along the Z-axis. Consequently, the wrist member 23 illustrated in FIG. 3 pivots in the directions indicated by the arrows B.

When the rotation, by the actuator, of the transmission member associated with the first gear 102 causes the first gear 102 to rotate, the second gear 103 engaged with the first gear 102 rotates about a rotational axis extending in the Z-axis direction. Consequently, the shaft 12 rotates in the directions indicated by the arrows A in conjunction with the rotation of the second gear 103.

[Bearing]

Referring again to FIG. 4, the end portion 11 further includes a plurality of bearings 161. The second pulley 43a, the fourth pulley 43b, and the fifth pulley 41 are mounted on the second connection 32 via the bearings 161. The first pulley 42a is mounted on the third connection 33 via the bearing 161. The third pulley 42b is mounted on the fourth connection 34 via the bearing 161. The pulley portions 25a and 25b illustrated in FIG. 3 are mounted on the first connection 31 via the bearings 161 not shown in FIG. 3.

Typical bearings can be used as the bearings 161. Those bearings which will be described below may also be employed.

Figure 9:
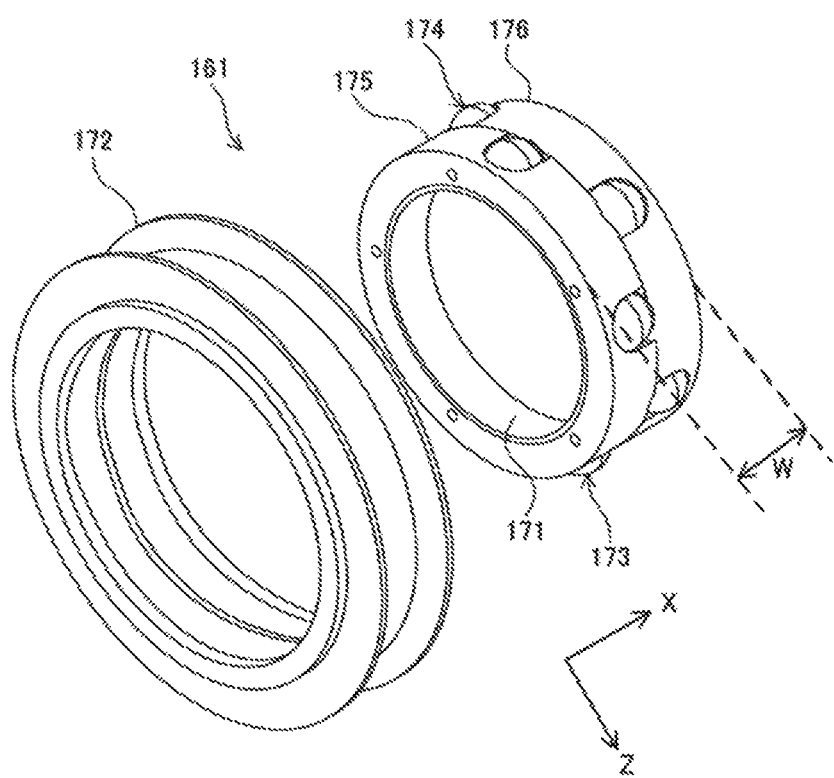
FIG. 9 is a diagram illustrating an exploded perspective view of a configuration of a bearing used in one or more embodiments.

FIG. 9 is a diagram illustrating an exploded perspective view of a configuration of a bearing used in one or more embodiments. In this example, the plurality of bearings 161 of the end portion 11 have the same configurations.

Referring to FIG. 9, the lower bearing 161 has an inner ring member 171, an outer ring member 172, a first ball group 173 having a plurality of balls, a second ball group 174 having a plurality of balls, a first retainer 175, and a second retainer 176. The inner ring member 171, the outer ring member 172, the first retainer 175, and the second retainer 176 have a ring shape.

The inner diameter of the outer ring member 172 is larger than the outer diameter of the inner ring member 171. The outer ring member 172 accommodates the inner ring member 171 such that the central axes of the outer and inner ring members 172 and 171 are aligned with each other.

The plurality of balls of the first ball group 173 are accommodated in the first retainer 175, where the balls are arranged at regular intervals in the circumferential direction of the first retainer 175. The plurality of balls of the second ball group 174 are accommodated in the second retainer 176, where the balls are arranged at regular intervals in the circumferential direction of the second retainer 176.

For example, the number of balls of the first ball group 173 and the number of balls of the second ball group 174 are the same. Each ball has the same size. The first and second retainers 175 and 176 have the same shape, and are brought into contact with each other, with the central axes of the inner and outer ring members 171 and 172 aligned with each other. The first and second retainers 175 and 176 are disposed between the inner and outer ring members 171 and 172.

The bearing 161 may be configured such that the first retainer 175 or the second retainer 176 is provided. In other words, the retainer may be provided on one side. However, the configuration in which the retainers are provided on both sides described above can disperse the load, applied to the retainers due to the rotation of the pulley portions 25a and 25b and the first to fifth pulleys 42a, 43a, 42b, 43b, and 41, more than the configuration in which the retainer is provided on one side. Consequently, the durability of the bearing 161 can be improved, and the medical treatment tool 4b can be used more times and for a longer period of time.

For example, the balls of the first ball group 173 and the balls of the second ball group 174 are alternately arranged in the circumferential direction of the first and second retainers 175 and 176. Part of each ball of the first ball group 173 is accommodated in the second retainer 176. Part of each ball of the second ball group 174 is accommodated in the first retainer 175.

This configuration can keep the width W of the bearing 161 from increasing. It is thus possible to prevent an increase in the friction at a contact portion between each of the plurality of bearings 161 and a corresponding one of the pulley portions 25a and 25b and first to fifth pulleys 42a, 43a, 42b, 43b, and 41.

An example has been described in which the bearings having the above configuration are used for all of the pulley portions 25a and 25b and the first to fifth pulleys 42a, 43a, 42b, 43b, and 41. However, the bearings having the above configuration may be used for some of the pulley portions. For example, the bearings having the above configuration may be used for only the first and third pulleys 42a and 42b which in many cases are used while tension is applied thereto from the elongate element 14.

The features described in this section can be summarized as follows.

[1] A bearing used in a medical treatment tool, the bearing including: an inner ring member having an annular shape; an outer ring member having an annular shape and a diameter larger than a diameter of the inner ring member; a first ball group including a plurality of first balls; a second ball group including a plurality of second balls; a first retainer having an annular shape and accommodating the plurality of first balls; and a second retainer having an annular shape and accommodating the plurality of second balls, wherein the first retainer and the second retainer are brought into contact with each other with central axes thereof aligned with each other, and are disposed between the inner ring member and the outer ring member.

[2] The bearing of item [1], wherein the first balls and the second balls are alternately arranged in a circumferential direction of the first retainer and the second retainer.

[3] The bearing of item [1] or [2], wherein part of each of the plurality of first balls is accommodated in the second retainer, and part of each of the plurality of second balls is accommodated in the first retainer.

[4] A medical treatment tool including: the bearing of any one of items [1] to [3]; an end effector including a pulley portion; an elongate element for operating the end effector, the elongate element being guided by the pulley portion; and a second pulley and a third pulley which guide the elongate element, wherein the bearing is attached to at least one of the second pulley or the third pulley.

[Fixation of Elongate Element and Respective Members of End Portion]

Figure 10:
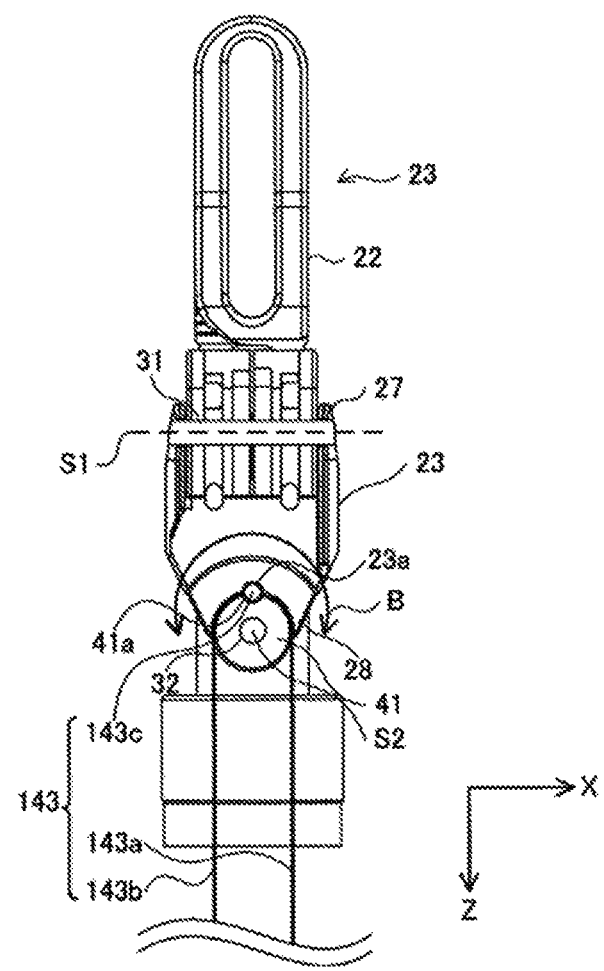
FIG. 10 is a diagram illustrating a connection relationship between a wrist member and a fifth pulley in the medical treatment tool according to one or more embodiments.

FIG. 10 is a diagram illustrating a connection relationship between the wrist member and the fifth pulley in the medical treatment tool according to one or more embodiments.

Referring to FIG. 10, as mentioned earlier, the fifth pulley 41 is attached to the wrist member 23 via the second connection 32 passing through the clevis 28 of the wrist member 23. Part of the circumference of the fifth pulley 41 is provided with a recessed portion 41a. The wrist member 23 is provided with a recessed portion 23a at a position opposed to the recessed portion 41a of the fifth pulley 41.

The elongate element 143 also has a projected portion 143c in addition to the wires 143a and 143b. The projected portion 143c is in a columnar shape, for example, and couples the wires 143a and 143b to each other. The recessed portion 41a of the fifth pulley 41 and the recessed portion 23a of the wrist member 23 are configured to be engageable with part of the projected portion 143c of the elongate element 143.

In the assembly of the medical treatment tool 4b, the worker brings the projected portion 143c of the elongate element 143 into engagement with the recessed portions 41a and 23a. Thus, the elongate element 143 can be easily fixed to the wrist member 23.

When the wire 143a or the wire 143b of the elongate element 143 is pulled in the Z-axis direction, with the elongate element 143 fixed to the wrist member 23, the projected portion 143c moves along the circumference of the fifth pulley 41 around the second axis S2, causing the fifth pulley 41 to rotate about the second axis S2 together with the projected portion 143c.

In this case, the recessed portion 23a, of the wrist member 23, engaged with the projected portion 143c moves along the circumference of the fifth pulley 41 around the second axis S2, causing the wrist member 23 to pivot in the directions indicated by arrows B, that is, to pivot circumferentially about the second axis S2.

Note that the elongate element 14 having the projected portion as described above may be used as a configuration for fixing the jaw 22 and the elongate element 141 to each other, and as a configuration for fixing the jaw 21 and the elongate element 142 to each other.

Figure 11:
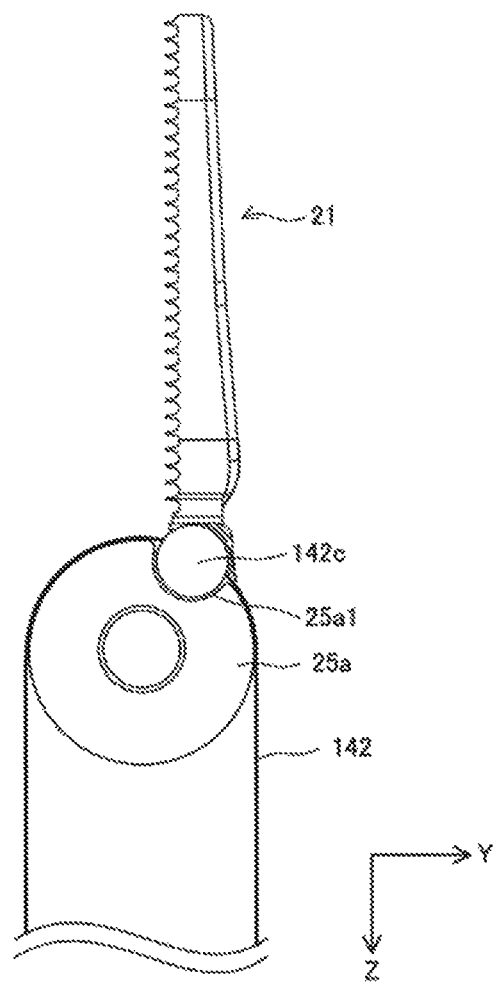
FIG. 11 is a diagram illustrating a connection relationship between a jaw and a pulley portion in the medical treatment tool according to one or more embodiments.

FIG. 11 is a diagram illustrating a connection relationship between a jaw and a pulley portion in the medical treatment tool according to one or more embodiments.

For example, as illustrated in FIG. 11, part of the circumference of the pulley portion 25a is provided with a recessed portion 25a1. Further, the elongate element 142 has a projected portion 142c formed into a columnar shape, for example. The recessed portion 25a1 of the pulley portion 25a is engaged with part of the projected portion 142c.

Note that the connection relationship between the jaw 22 and the pulley portion 25b is the same as, or similar to, the connection relationship between the jaw 21 and the pulley portion 25a illustrated in FIG. 11.

In this configuration, the elongate element 142 can be fixed to the jaw 21 in the assembly of the end portion 11 by bringing the recessed portion 25a1 into engagement with the projected portion 142c. The assembly of the end portion 11 can thus be facilitated.

The shape of the projected portions 142c and 143c is not limited to the columnar shape. Further, the corresponding recessed portions 41a and 25a1 do not have to be configured as cutouts obtained by cutting a portion out of a round shape. As long as the projected portion and the recessed portion can be engaged with each other, the projected portions 142c and 143c may have a cubic shape, and the recessed portions 41a and 25a1 may be configured as cutouts in a shape engageable with the cubic shape.

(Variations)

Figure 12:
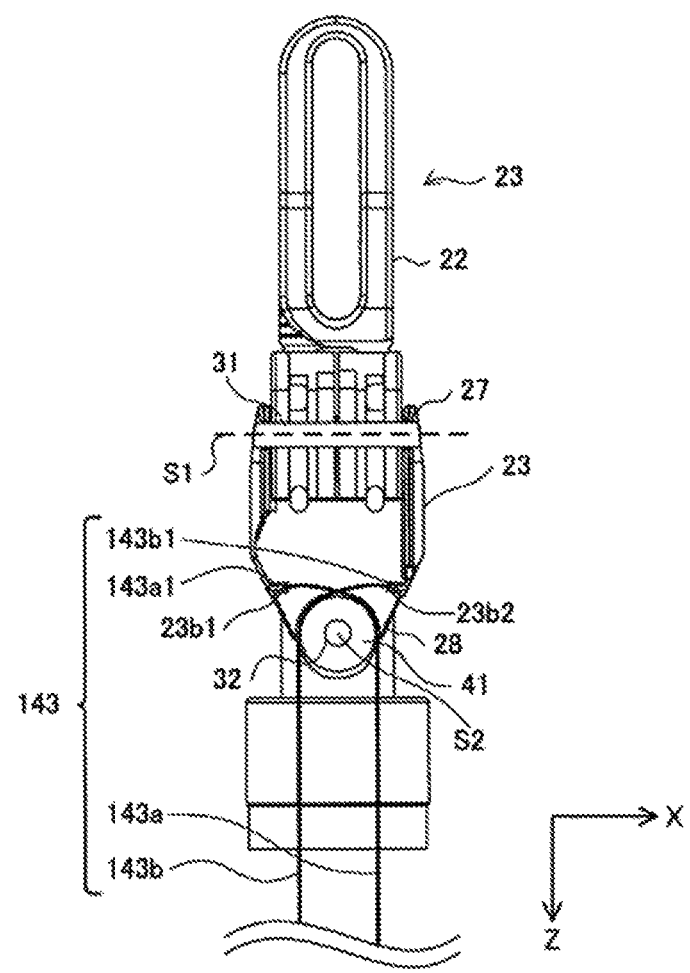
FIG. 12 is a diagram illustrating a variation of the connection relationship between the wrist member and the fifth pulley.

FIG. 12 is a diagram illustrating a variation of the connection relationship between the wrist member and the fifth pulley.

As illustrated in FIG. 12, the elongate element 143 may have columnar wider portions 143a1 and 143b1 at the ends of the wires 143a and 143b, instead of having the projected portion 143c. In this case, the wider portions 143a1 and 143b1 are brought into engagement with slots 23b1 and 23b2 provided at the wrist portion 23.

However, in such a configuration, the elongate element 143 may protrude into the body cavity in the unlikely event of breakage of the elongate element 143. Further, in such a configuration, the wider portions 143a1 and 143b1 need to be engaged with the slots 23b1 and 23b2, respectively, in order to fix the elongate element 143 to the wrist member 23.

On the other hand, the configuration as illustrated in FIG. 10 can prevent the elongate element 143 from protruding into the body cavity even in the unlikely event of breakage of the elongate element 143. Moreover, such a configuration can facilitate fixing the elongate element 143 to the wrist member 23. It is therefore preferable to fix the elongate element 143 by the configuration as illustrated in FIG. 10.

Note that it is not essential to apply the configuration as illustrated in FIG. 10 to the end portion 11 which has been described so far, and it is not intended to exclude the adoption of the configuration as illustrated in FIG. 12.

The features described in this section can be summarized as follows.

[1] A medical treatment tool including: a wrist member extending in a particular direction; an end effector mounted on a first end, in the particular direction, of the wrist member via a first connection; a shaft; an elongate element for operating the wrist member; and a pulley which guides the elongate element, wherein a second end of the wrist member, opposite to the first end in the particular direction, is mounted on an end of the shaft via a second connection, the pulley is rotatable about the second connection, the elongate element has a projected portion, and the projected portion engages with both of a recessed portion formed at the pulley and a recessed portion formed at the second end of the wrist member.

[2] A medical treatment tool including: an end effector having a pulley portion; and an elongate element for operating the end effector, the elongate element being guided by the pulley portion, wherein the elongate element has a projected portion, and the projected portion engages with a recessed portion formed at the pulley.

[Measures Against Extension of Elongate Element]

Figure 13:
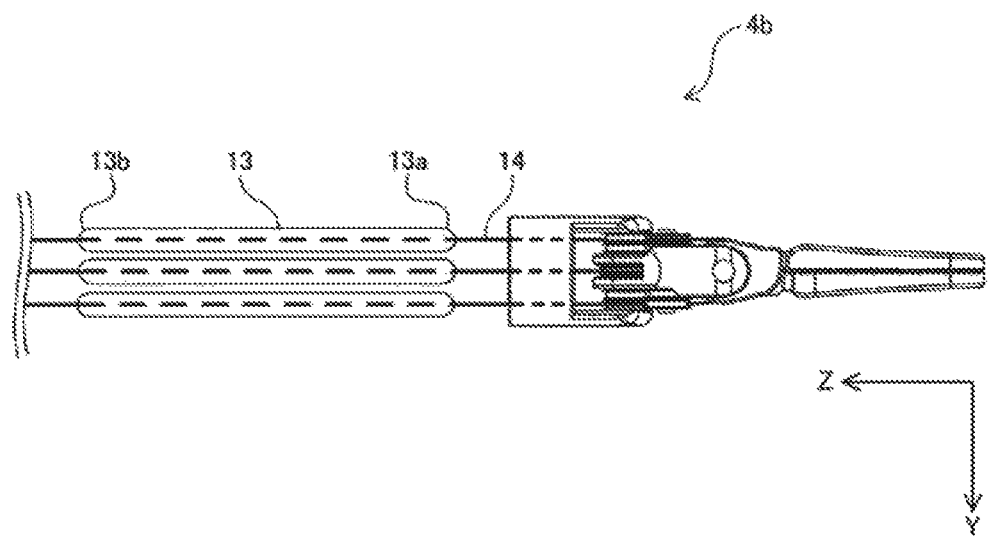
FIG. 13 is a diagram illustrating a first example of the configuration of the elongate element in the medical treatment tool according to one or more embodiments.

FIG. 13 is a diagram illustrating a first example of the configuration of the elongate element in the medical treatment tool according to one or more embodiments.

Referring to FIG. 13, the medical treatment tool 4b includes a rigid tube 13 which covers part of the elongate element 14. The elongate element 14 could be extended due to repeated use for a long term, because the elongate element 14 is made of a material, such as stainless steel or tungsten, and formed, for example, into a wire or a cable having a diameter of 0.45 mm.

Thus, covering at least part of the elongate element 14 with the rigid tube 13 which, compared to the elongate element 14, is sufficiently hard and does not extend, substantially shortens the length of the extendable elongate element 14, and reduces the effect caused by the extension of the elongate element 14. The rigid tube 13 is made of a material, such as stainless steel, and is formed into a pipe having a diameter of about 1.06 mm. Thus, the rigid tube 13 is not extended even if the rigid tube 13 is used for a long term.

At least one of a first end 13a or a second end 13b of the rigid tube 13 in the longitudinal direction thereof according to the present example configuration is chamfered. Specifically, both of the first and second ends 13a and 13b are formed to have round smooth faces, or tapered.

This configuration may prevent the elongate element 14 from being damaged by an edge of the rigid tube 13 which could come into contact with, and cause damage to, the elongate element 14, even when the end portion 11 makes a complicated movement through the actuation of the elongate element 14.

Figure 14:
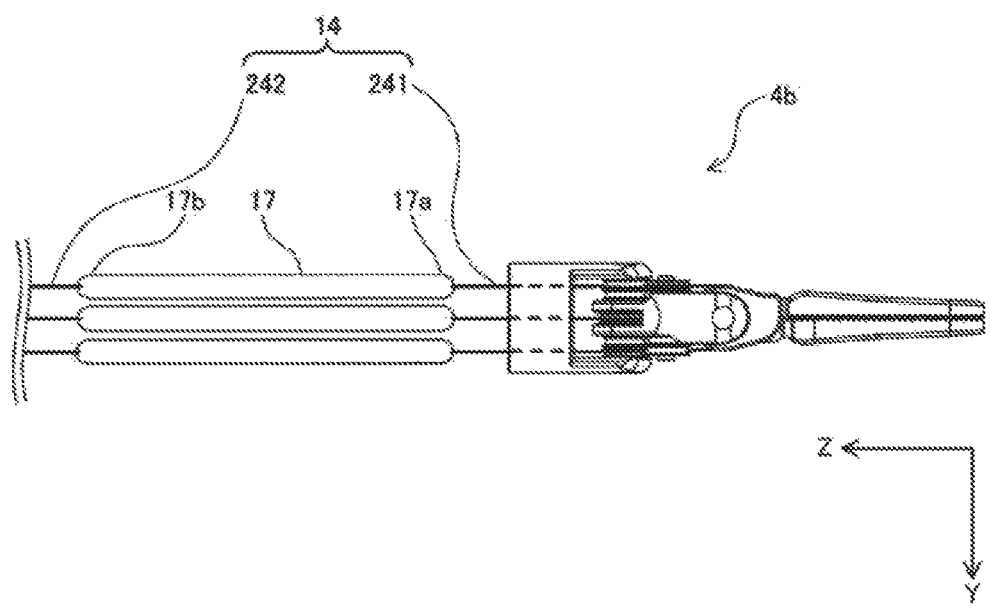
FIG. 14 is a diagram illustrating a second example of the configuration of the elongate element in the medical treatment tool according to one or more embodiments.

FIG. 14 is a diagram illustrating a second example of the configuration of the elongate element in the medical treatment tool according to one or more embodiments.

The medical treatment tool 4b illustrated in FIG. 14 employs a rod 17, made of a hard material, at an intermediate portion of the elongate element 14, instead of the rigid tube 13 covering the elongate element 14. In this case, for example, the elongate element 14 has an end portion wire 241 on the negative side of the Z-axis and an activation mechanism wire 242 on the positive side of the Z-axis.

The end portion wire 241 is coupled to a first longitudinal end 17a of the rod 17. The activation mechanism wire 242 is coupled to a second longitudinal end 17b of the rod 17. At least one of the first or second ends 17a and 17b of the rod 17 is chamfered. Specifically, both of the first and second ends 17a and 17b are formed to have round smooth faces, or tapered.

The elongate element 14 is wound around the activation member 101 mounted on the activation mechanism 15 illustrated in FIG. 8, so that tension on the elongate element 14 is adjusted. Since the tension is kept on the elongate element 14, the elongate element 14 may be extended in the direction in which the tension is applied, that is, in the Z-axis direction. On the other hand, the configuration employing the rod 17 as described above can shorten the length of the elongate element 14 by the length of the rod 17, which means that the length of extension of the elongate element 14 can be reduced.

The features described in this section can be summarized as follows.

[1] A medical treatment tool including: an end effector having a pulley portion; an elongate element for operating the end effector, the elongate element being guided by the pulley portion; and an activation member which actuates the elongate element, wherein a portion of the elongate element is covered with a rigid tube, and an edge of at least one of both longitudinal ends of the rigid tube is chamfered.

[2] The medical treatment tool of item [1], wherein the edge of at least one of both longitudinal ends of the rigid tube is tapered.

Note that it is not essential to apply these features to the end portion 11 which has been described so far, and it is not intended to exclude the employment of the rigid tube or the rod not chamfered.

The embodiment disclosed herein is meant to be illustrative in all respects and should not be construed to be limiting in any manner. The scope of one or more embodiments is defined not by the above description, but by the scope of claims, and intended to include all modifications within equivalent meaning and scope to those of the claims.

What is claimed is:

1. A medical treatment tool comprising:
an end effector including a first pulley portion and a first finger portion extending from the first pulley portion, the first pulley portion being provided with a groove extending in a circumferential direction of the first pulley portion;
a wrist member which extends in a particular direction and on which the first pulley portion is rotatably mounted via a first connection at a first end of the wrist member in the particular direction;
a shaft which has a shaft axis and on which a second end of the wrist member, opposite to the first end in the particular direction, is rotatably mounted via a second connection;
a first pulley mounted on the wrist member; and
a second pulley which is located closer to the second end of the wrist member than the first pulley with respect to the particular direction, and which has a rotational axis parallel to a second axis defined by the second connection,
wherein the first pulley portion is located closer to a first end of the first connection than a second end of the first connection, opposite to the first end of the first connection, with respect to a direction of a first axis defined by the first connection,
wherein the first pulley, the second pulley, and the first finger portion stay on one side of a plane defined by the shaft axis and the first axis when the wrist member is in a position in which the particular direction of the wrist member is parallel to the shaft axis,
wherein a rotational axis of the first pulley and the rotational axis of the second pulley intersect with the plane, and
wherein the first pulley is located closer to the second end of the first connection than the first pulley portion is, with respect to the direction of the first axis, wherein the first pulley and the first pulley portion do not overlap with each other as seen in a direction orthogonal to the direction of the first axis.

2. The medical treatment tool of claim 1, further comprising:
a third pulley mounted on the wrist member; and
a fourth pulley which is located closer to the second end of the wrist member than the third pulley with respect to the particular direction, and which has a rotational axis parallel to the second axis,
wherein the end effector further comprises:
a second pulley portion, the second pulley portion being located closer to the second end of the first connection than the first end of the first connection with respect to the first axis, and being provided with a groove extending in a circumferential direction of the second pulley portion; and
a second finger portion extending from the second pulley portion,
wherein the third pulley, the fourth pulley, and the second finger portion are provided on the other side of the plane, opposite to the one side of the plane,
wherein a rotational axis of the third pulley and the rotational axis of the fourth pulley intersect with the plane, and
wherein the third pulley is located closer to the first end of the first connection than the second pulley portion is, with respect to the direction of the first axis.

3. The medical treatment tool of claim 2, wherein
the third pulley and the second pulley portion do not overlap with each other as seen in a direction orthogonal to the direction of the first axis.

4. The medical treatment tool of claim 1, further comprising:
a first elongate element for operating the end effector, the first elongate element being guided by the first pulley portion, and the first elongate element being further guided to a space between the first pulley and the second pulley from near the first end of the first connection and passing through said space.

5. The medical treatment tool of claim 1, wherein
a length from the first connection to the second connection is less than 8 mm.

6. The medical treatment tool of claim 5, further comprising:
a first elongate element for operating the end effector; and
a second elongate element for operating the wrist member.

7. The medical treatment tool of claim 6, wherein
at least a portion of the first elongate element and the second elongate element is covered with a rigid tube, an edge of at least one of both longitudinal ends of the rigid tube being chamfered.

8. The medical treatment tool of claim 6, further comprising:
a fifth pulley which guides the second elongate element and is rotatable about the second axis,
wherein the second elongate element has a projected portion, the projected portion engaging with both of a recessed portion formed at the fifth pulley and a recessed portion formed at the second end of the wrist member.

9. The medical treatment tool of claim 6, wherein
the first elongate element has a projected portion, the projected portion engaging with a recessed portion formed at the end effector.

10. The medical treatment tool of claim 6, further comprising:
a first activation member and a second activation member which actuate the first elongate element and the second elongate element, respectively,
wherein each of the first activation member and the second activation member includes a receiving member which engages with a transmission member.

11. A surgical system comprising:
the medical treatment tool of claim 10; and
a manipulator including an actuator which actuates the transmission member.

12. The medical treatment tool of claim 1, further comprising:

a first elongate element for operating the end effector; and a second elongate element for operating the wrist member.

13. The medical treatment tool of claim 12, wherein
at least a portion of the first elongate element and the second elongate element is covered with a rigid tube, an edge of at least one of both longitudinal ends of the rigid tube being chamfered.

14. The medical treatment tool of claim 12, comprising:
a fifth pulley which guides the second elongate element and is rotatable about the second axis,
wherein the second elongate element has a projected portion, the projected portion engaging with both of a recessed portion formed at the fifth pulley and a recessed portion formed at the second end of the wrist member.

15. The medical treatment tool of claim 12, wherein
the first elongate element has a projected portion, the projected portion engaging with a recessed portion formed at the end effector.

16. The medical treatment tool of claim 1, further comprising:
a bearing,
wherein the bearing comprises
an inner ring member having an annular shape,
an outer ring member having an annular shape and a diameter larger than a diameter of the inner ring member,
a first ball group including a plurality of first balls,
a second ball group including a plurality of second balls,
a first retainer having an annular shape and accommodating the plurality of first balls, and
a second retainer having an annular shape and accommodating the plurality of second balls, and
wherein the first retainer and the second retainer are brought into contact with each other with central axes thereof aligned with each other, and are disposed between the inner ring member and the outer ring member.

17. The medical treatment tool of claim 16, wherein
the first balls and the second balls are alternately arranged in a circumferential direction of the first retainer and the second retainer.

18. The medical treatment tool of claim 16, wherein
part of each of the plurality of first balls is accommodated in the second retainer, and
part of each of the plurality of second balls is accommodated in the first retainer.

19. The medical treatment tool of claim 16, wherein
the bearing is provided for the first pulley mounted on the wrist member.

20. A medical treatment tool comprising:
an end effector including a first pulley portion and a first finger portion extending from the first pulley portion, the first pulley portion being provided with a groove extending in a circumferential direction of the first pulley portion;
a wrist member on which the first pulley portion is rotatably mounted via a first connection at a distal end of the wrist member;
a shaft which has a shaft axis and on which a proximal end of the wrist member, is rotatably mounted via a second connection;
a first pulley mounted on the wrist member; and
a second pulley which is located closer to the proximal end of the wrist member than the first pulley, and which has a rotational axis parallel to a second axis defined by the second connection,
wherein the first pulley portion is located closer to a first end of the first connection than a second end of the first connection, opposite to the first end of the first connection, with respect to a direction of a first axis defined by the first connection,
wherein the first pulley, the second pulley, and the first finger portion stay on one side of a plane defined by the shaft axis and the first axis when the wrist member is in a position in which a longitudinal direction of the wrist member is parallel to the shaft axis,
wherein a rotational axis of the first pulley and the rotational axis of the second pulley intersect with the plane, and
wherein the first pulley is located closer to the second end of the first connection than the first pulley portion is, with respect to the direction of the first axis, wherein the first pulley and the first pulley portion do not overlap with each other as seen in a direction orthogonal to the direction of the first axis.

* * * * *